United States Patent [19]

Funk, Jr.

[11] Plant 4,223

[45] Mar. 14, 1978

[54] KENTUCKY BLUEGRASS

[75] Inventor: Cyril Reed Funk, Jr., East Brunswick, N.J.

[73] Assignee: The O. M. Scott & Sons Company, Marysville, Ohio

[21] Appl. No.: 775,264

[22] Filed: Mar. 7, 1977

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—J. B. Raden; H. J. Holt

[57] ABSTRACT

A variety of Kentucky bluegrass which exhibits good resistance to common lawn grass diseases including leaf spot, leaf rust, stripe smut and powdery mildew, has an attractive, rich, dark green color and a turf-type growth habit.

3 Drawing Figures

SUMMARY OF THE VARIETY

This invention relates to a new and distinct variety of *Poa pratensis* which has been designated P-101 Kentucky bluegrass.

The variety was originated by crossing an upatentedselection identified in our breeding records as Bellevue with Anheuser Dwarf (U.S. Plant Pat. No. 3,135), Bellevue being the seed parent and Anheuser Dwarf the pollen parent. As a result of this breeding, I have produced and asexually propagated by rhizomes, tillers and disseminules, a variety which is distinct from each of its parents and from all other varieties of which I am aware.

Asexual reproduction of P-101 by propagules (tillers and rhizomes) and by disseminules (modified caryopses produced by agamospermy) has consistently produced progeny plants indistinguishable from the mother plant.

The novel characteristics of the P-101 Kentucky bluegrass variety reside particularly in its attractive, rich, dark green color which can be maintained throughout the entire growing season, moderately wide leaf blades, turf-type growth habit, good resistance to common turf diseases including leaf spot, leaf rust, stripe smut and powdery mildew and its ability to produce a high quality turf. Specifically, P-101 exhibits the following unique combination of characteristics:

1. Good resistance to the leaf spot and crown rot disease caused by the fungus, *Helminthosporium vagans;*

2. Good resistance to the stripe smut disease caused by the fungus, *Ustilago striiformis;*

3. Good resistance to powdery mildew caused by the fungus, *Erysiphe graminis;*

4. Good resistance to the leaf rust disease caused by the fungus, *Puccinia poae-nemoralis.*

5. An attractive, rich, dark green color which can be maintained throughout the entire growing season;

6. Good rhizome and tiller development under turf maintenance producing a turf of moderate density and good horizontal spreading ability.

7. A leafy turf-type growth habit tolerant of moderately close mowing;

8. Moderately wide leaf blades;

9. Large spikelets; and

10. Good turf performance, as evidenced by consistently high performance scores in tests in New Jersey and Ohio.

In comparison with its seed parent, Bellevue, the new variety has wider leaves, larger spikelets, a darker green color, maintains a more leafy turf during late spring and has better resistance to stripe smut and powdery mildew.

In comparison with its pollen parent, Anheuser Dwarf, the new variety has taller, more upright culms and better early spring color.

In comparison with its sister selection, P-72 (U.S. Plant Pat. No. 3,782), the new variety is taller, has fewer panicles and produces a more leafy turf in late spring.

DETAILED DESCRIPTION OF THE VARIETY

Figure 1:
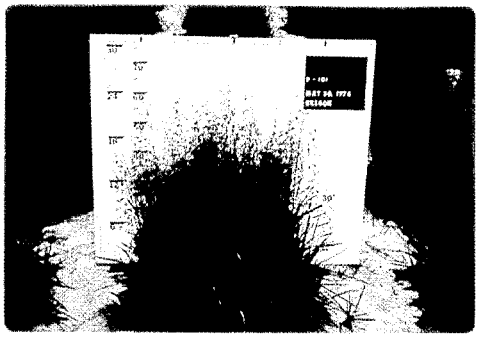
FIG. 1 is a photograph of a P-101 Kentucky bluegrass plant after completion of anthesis.
Figure 2:
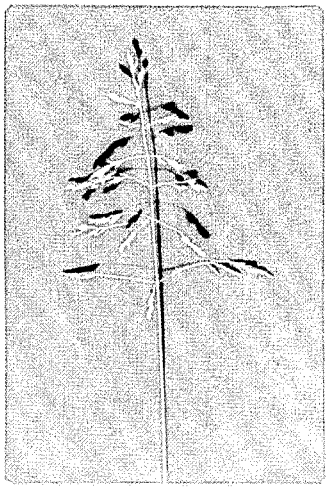
FIG. 2 shows a typical mature P-101 panicle.
Figure 3:
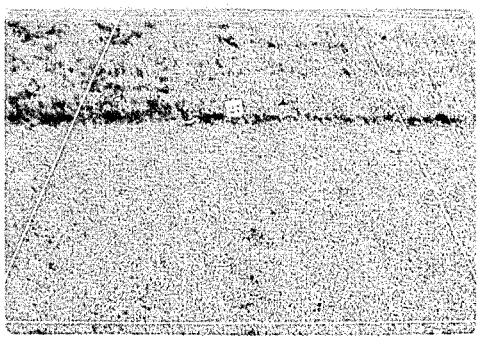
FIG. 3. shows an established plot of P-101 Kentucky bluegrass maintained under turf conditions in which the front half has been cut at $\frac{3}{4}$ inches, the back half at $1\frac{3}{4}$ inches.

P-101 Kentucky bluegrass (*Poa pratensis* L.) is perennial with creeping rhizomes forming a moderately dense turf. Culms are quite erect with only a slight bend at lower nodes, tufted averaging 74 cm tall when undisturbed by clipping. Leaves are dark green, averaging 4.2 mm wide; the blades are hairless on both sides, initially folded but then opening out with a boat-shaped apex. Ligules are membranous and covered with fine hairs, edge of collar is fringed in fine hairs. The flag leaf averages 45 mm in length. Panicles at time of anthesis are green, lightly tinged with purple, slightly nodded at the tip, pyrimidal and open averaging 99 mm long. Lower branches are mostly perpendicular to the main panicle axis, lowest cluster of branches usually in a whorl of 3 to 4 (average 3.5). Spikelets are ovate, compressed, 4.7 to 6.8 mm long (average 5.7), usually 4 to 5-flowered (average 4.4), breaking up at maturity beneath each lemna. Glumes persistent, pointed, unequal, rough on the keels; lower mostly 1-nerved, ovate averaging 3.1 mm long, upper 3-nerved, ovate to elliptic averaging 3.5 mm long. Lemmas overlapping, 5-nerved, oblong or ovate in side view, pointed tip, hair on the keel and nerves to the middle, long fine crinkled hair at the base and on the lower margin. Paleas about as long as the lemmas with 2 rough keels. Grain tightly enclosed in the lemma and palea.

Since environmental conditions such as soil and climate influence morphological characters to some degree, the morphological characteristics will vary somewhat. Morphological characteristics of P-101 are compared with other Kentucky bluegrass varieties in Table 1.

Table 1.

Morphological comparison of P-101 and other bluegrass varieties at Adelphia, New Jersey

| Variety | Plant height cm | Plant diameter cm | Leaf Blade width mm | Flag leaf length mm | Number of panicles per plant | panicle color[1] | Panicle erect or nodding[2] | Number of branches at lowest panicle node | Panicle length mm |
|---|---|---|---|---|---|---|---|---|---|
| P-101 | 74 | 25 | 4.2 | 45 | 78 | 1.5 | 2.0 | 3.5 | 99 |
| P-72 | 66 | 26 | 4.0 | 47 | 199 | 1.5 | 1.5 | 3.9 | 102 |
| Delta | 73 | 17 | 2.6 | 67 | 196 | 2.0 | 1.0 | 4.8 | 100 |
| Geary | 80 | 24 | 2.9 | 80 | 177 | 3.0 | 3.0 | 4.0 | 134 |
| Newport | 79 | 30 | 4.8 | 77 | 246 | 2.5 | 2.0 | 4.3 | 105 |
| Palouse | 79 | 24 | 3.0 | 93 | 151 | 3.0 | 3.5 | 4.4 | 92 |
| Anheuser Dwarf | 67 | 30 | 5.1 | 51 | 109 | 3.0 | 2.5 | 3.4 | 96 |
| Eelturf | 70 | 35 | 3.0 | 58 | 201 | 2.0 | 2.0 | 4.0 | 104 |
| Fylking (U.S. Pat. No. 2887) | 60 | 34 | 4.0 | 68 | 164 | 3.5 | 5.0 | 4.9 | 118 |
| Merion | 70 | 24 | 4.3 | 69 | 280 | 2.0 | 1.5 | 3.5 | 102 |
| Pennstar | 59 | 34 | 3.7 | 66 | 132 | 3.5 | 4.0 | 4.5 | 106 |

[1]Scale: 0 = green; 5 = purple
[2]Scale: 1 = erect; 5 = nodding

The new variety has exhibited consistently high turf performance ratings at New Brunswick, N. J. and Marysville, Ohio. Overall turf performance ratings for P-101 and other bluegrasses are presented in Tables 2 and 3.

Table 2.

Turf performance ratings of P-101 and other bluegrass varieties at New Brunswick, New Jersey

| Variety | Turf Performance Score 9 = best | | | | | |
|---|---|---|---|---|---|---|
| | 1966 | 1967 | 1968 | 1969 | 1970 | Ave. |
| P-101 | 7.8 | 8.5 | 8.4 | 7.9 | 7.0 | 7.9a* |
| Anheuser Dwarf | 7.6 | 7.3 | 7.5 | 6.9 | 7.6 | 7.4a |
| Fylking | 6.9 | 6.8 | 8.0 | 7.6 | 7.2 | 7.3a |
| Pennstar | 6.9 | 6.8 | 7.9 | 7.1 | 7.2 | 7.2a |
| Belturf | 6.2 | 5.9 | 7.4 | 7.0 | 6.2 | 6.5b |
| Bellevue | 6.4 | 6.7 | 6.9 | 5.9 | 5.7 | 6.3b |
| Merion | 6.3 | 6.1 | 6.8 | 4.9 | 4.1 | 5.6c |
| Delta | 4.5 | 4.2 | 5.2 | 4.9 | 4.5 | 4.7d |

*Values within a column followed by the same letter do not differ at the five percent probability level.

Table 3.

Relative comparison of P-101 and other bluegrass varieties growing under natural shade at Marysville, Ohio.

| Variety | Turf quality score 9 = best | | | |
|---|---|---|---|---|
| | May 16 | July 1 | September 30 | Ave. |
| P-101 | 7.7 | 7.7 | 7.8 | 7.7 |
| P-72 | 7.9 | 6.6 | 6.9 | 7.1 |
| Merion | 6.2 | 6.2 | 5.7 | 6.0 |
| Fylking | 4.7 | 4.7 | 4.1 | 4.5 |
| Pennstar | 4.8 | 4.1 | 3.0 | 3.8 |
| Park | 3.0 | 4.5 | 3.3 | 3.6 |

The new variety has a dark green color which can be maintained throughout the growing season. Color rating comparisons of P-101 and other bluegrasses grown at Accokeek, Md., are presented in Table 4.

Table 4.

Color rating comparisons of P-101 and other bluegrass varieties grown at Accokeek, Maryland.

| Variety | Color rating (10 = darkest green) | | | | | | | |
|---|---|---|---|---|---|---|---|---|
| | Feb. 14 | Apr. 1 | May 22 | June 15 | July 22 | Sept. 5 | Nov. 22 | Ave. |
| P-101 | 9.0 | 8.0 | 9.0 | 9.0 | 8.0 | 8.5 | 8.0 | 8.5 |

Table 4.-continued

Color rating comparisons of P-101 and other bluegrass varieties grown at Accokeek, Maryland.

| Variety | Color rating (10 = darkest green) | | | | | | | |
|---|---|---|---|---|---|---|---|---|
| | Feb. 14 | Apr. 1 | May 22 | June 15 | July 22 | Sept. 5 | Nov. 22 | Ave. |
| P-72 | 8.0 | 8.0 | 8.0 | 8.0 | 9.0 | 8.0 | 9.9 | 8.4 |
| Sydsport | 6.5 | 6.0 | 6.0 | 7.5 | 8.0 | 8.0 | 6.8 | 7.0 |
| Windsor | 7.0 | 6.0 | 5.5 | 7.0 | 7.0 | 8.3 | 6.5 | 6.8 |
| Nu Dwarf | 2.0 | 6.0 | 6.0 | 7.0 | 7.0 | 8.0 | 6.5 | 6.1 |
| Common Kentucky | 4.0 | 7.0 | 5.0 | 6.0 | 7.0 | 7.0 | 6.0 | 6.0 |

The new variety is moderately aggressive with good horizontal spreading ability as shown by measurements presented in Table 5.

Table 5.

Aggressiveness of various bluegrass varieties as measured by their ability to spread under conditions of close mowing and competition from other bluegrasses at New Brunswick, New Jersey.

| Variety | Amount of encroachment into adjacent bluegrass varieties (inches) |
|---|---|
| P-101 | +10.0* |
| Belturf | + 8.0 a |
| Bellevue | + 3.0 b |
| Pennstar | + 2.5 b |
| Fylking | + 2.5 b |
| Anheuser Dwarf | + 2.0 b |
| Merion | − 1.5 c |
| Windsor | − 1.5 c |
| Delta | − 3.0 c |

*Values within a column followed by the same letter do not differ at the five percent probability level.

Comparisons of P-101 and other bluegrasses for resistance to leaf spot and crown rot caused by the fungus *Helmintosporium vagans,* stripe smut caused by the fungus *Ustilago striiformis,* powdery mildew caused by the fungus *Erysiphe gramins* and leaf rust caused by the fungus *Puccinia poae-nemoralis* are presented in Tables 6, 7, 8, 9, 10 and 11.

Table 6.

Relative comparison of leaf spot and crown rot disease incidence of P-101 and other bluegrasses at New Brunswick, New Jersey.

| Variety | percent disease damage |
|---|---|
| P-101 | 2 a* |
| Anheuser Dwarf | 2 a |
| Merion | 5 b |
| Fylking | 6 b |
| Pennstart | 6 b |

Table 6.-continued

Relative comparison of leaf spot and crown rot disease incidence of P-101 and other bluegrasses at New Brunswick, New Jersey.

| Variety | percent disease damage |
|---|---|
| Bellevue | 10 b |
| Belturf | 20 c |
| Delta | 70 d |

*Values within a column followed by the same letter do not differ at the five percent probability level.

Table 7.

Relative comparison of leaf spot disease incidence on P-101 and other bluegrass varieties under natural shade at Marysville, Ohio.

| | Percent leafspot | | | |
|---|---|---|---|---|
| Variety | May 16 | July 1 | September 30 | Ave. |
| P-101 | 20 | 17 | 8 | 15 |
| P-72 | 20 | 23 | 9 | 17 |
| Merion | 33 | 23 | 15 | 24 |
| Fylking | 38 | 37 | 25 | 33 |
| Pennstar | 34 | 39 | 40 | 38 |
| Park | 59 | 44 | 26 | 43 |

Table 8.

Relative comparison of strip smut disease incidence of P-101 and other bluegrasses at New Brunswick, N.J.

| Variety | Stripe smut infected tillers per square foot of turf |
|---|---|
| Anheuser Dwarf | 0 a* |
| Pennstar | 0 a |
| Fylking | 0 a |
| P-101 | 2 a |
| Bellevue | 11 b |
| Delta | 11 b |
| Merion | 228 c |

*Values within a column followed by the same letter do not differ at the five percent probability level.

Table 9.

Reaction of Kentucky bluegrass varieties to powdery mildew disease under greenhouse conditions at New Brunswick, New Jersey.

| Variety | Mildew rating 9 = most disease |
|---|---|
| A-20 | 0.0 a* |
| P-101 | 0.7 b |
| Newport | 0.8 b |
| A-34 | 1.8 c |
| Sodco | 2.0 c |
| Fylking | 3.9 d |
| Pennstar | 4.2 d |
| Belturf | 4.3 d |
| Merion | 6.9 e |

*Values followed by the same letter do not differ significantly at the five percent probability level.

TABLE 10.

Relative comparison of powdery mildew disease incidence on P-101 and other bluegrass varieties under natural shade at Marysville, Ohio.

| Variety | Percent mildew |
|---|---|
| P-101 | 2.7 |
| A-34 | 6.7 |
| P-72 | 7.3 |
| Nugget | 28.3 |
| Common Kentucky | 70.0 |
| Pennstar | 80.0 |
| Windsor | 86.7 |
| Merion | 93.3 |

Table 11.

Relative comparison of leaf rust disease level for P-101 and other bluegrass varieties at Adelphia, New Jersey.

| Variety | Rust disease rating* |
|---|---|
| P-101 | 0.8 a** |
| Pennstar | 1.5 b |
| Fylking | 1.5 b |
| Prato | 2.0 b |
| Newport | 3.5 c |
| Merion | 3.5 c |
| Vantage | 7.5 d |

*Rating Scale: 0 = no rust; 9 = disease most severe

**Values followed by the same letter do not differ significantly at the five percent probability level.

The new variety is medium late in maturity as indicated by relative comparison of flowering dates presented in Table 12.

Table 12.

Date of initiation of anthesis of Kentucky bluegrass varieties at Adelphia, New Jersey.

| Variety | Date flowers first open | |
|---|---|---|
| Kenblue* | May 18 to | May 24 |
| Delta | May 20 | a** |
| Nugget | May 23 | b |
| Newport | May 25 | c |
| Fylking | May 26 | cd |
| Pennstar | May 26 | cd |
| Galaxy | May 27 | de |
| Majestic | May 27 | de |
| Bonnieblue | May 27 | de |
| P-101 | May 27 | de |
| Anheuser Dwarf | May 28 | ef |
| Merion | May 29 | fg |
| Adelphi | May 30 | g |
| Glade | May 30 | g |
| Brunswick | June 2 | h |

*Kenblue is a mixture of different bluegrass types.

**Parts followed by the same letter do not differ statistically at the five percent probability level.

I claim:

1. A new and distinct variety of Kentucky bluegrass plant, substantially as shown and described, characterized by good resistance to many important lawn grass diseases, good turf performance, an attractive dark green color, good rhizome and tiller development and moderately wide leaves.

* * * * *